United States Patent [19]
Haseltine et al.

[11] Patent Number: 6,033,902
[45] Date of Patent: Mar. 7, 2000

[54] VECTOR COMPRISING A REPLICATION COMPETENT HIV-1 PROVIRUS AND A HETEROLOGOUS GENE

[75] Inventors: William A. Haseltine, Cambridge; Ernest Terwilliger, Boston, both of Mass.

[73] Assignee: Dana-Farber Cancer Institute, Boston, Mass.

[21] Appl. No.: 07/987,572

[22] Filed: Dec. 8, 1992

Related U.S. Application Data

[63] Continuation of application No. 07/249,918, Sep. 27, 1988, abandoned.

[51] Int. Cl.[7] .......................... C12N 15/86; C12N 15/49
[52] U.S. Cl. .................................... 435/320.1; 435/235.1
[58] Field of Search .............................. 435/320.1, 235.1

[56] References Cited

FOREIGN PATENT DOCUMENTS

| | | |
|---|---|---|
| 0187041 | 7/1986 | European Pat. Off. . |
| 0219106 | 4/1987 | European Pat. Off. . |
| 0276591 | 8/1988 | European Pat. Off. . |
| 0293181 | 11/1988 | European Pat. Off. . |
| 8803562 | 5/1988 | WIPO . |

OTHER PUBLICATIONS

Barre–Sinoussi, et al. Science 220:868–871 (1983).
Gallo, et al. Science 224 : 500–503 (1984).
Levy, et al. Science 225:840–842 (1984).
Popovic, et al. Science 224:497–500 (1984).
Sarngadharan et al., Science 224:506–508 (1984).
Siegal; et al. N. Engl. J. Med. 305:1439–1444 (1981).
Zagury, et al. Science 231:850–823 (1986).
Ratner, et al., Nature 313:277–284 (1985).
Sanchez–Pescador, et al., Science 227:484–492 (1985).
Muesing, et al., Nature 313:450–457 (1985).
Wain–Hobson, et al., Cell 40:9–17 (1985).
Sodroski, et al:, Science 231:1549–1553 (1986).
Arya, et al., Science 229:69–73 (1985).
Sodroski, et al., Science 227:171–173 (1985).
Feinberg, et al. Cell 46:807–817 (1986).
Rosen, C.A., et al., Nature 319:555–559 (1986).
Sodroski, et al., Nature 321:412–417 (1986).
Luciw, P.A., et al. PNAS 84:1434–1438 (1987).
Fisher, A.G. et al (1985) Nature 316:262–265.
Kantoff, P.W. et al. (1986) Proc. Natl. Acad. Sci. USA 83:6563–6567.
Mariman, E.C.M. (1985) Nature 318:414.
Tellier, R. et al. (1985) Nature 318:414.
E.F. Terwilliger et al. (1989) Proc. Natl. Acad. Sci. USA 86:3857–3861.
B.R. Cullen et al. (1990) Virology 178:1–5.
S. Wain–Hobson (1989) AIDS 3 (Suppl. 1):513–518.
W. A Haseltine (1988) J. Acquired Imm. Def. Syn. 1:217–240.

*Primary Examiner*—Johnny F. Railey, II
*Attorney, Agent, or Firm*—Ronald I. Eisenstein; David S. Resnick; Nixon Peabody LLP

[57] ABSTRACT

A vector comprising an HIV segment and a heterologous gene segment, which produces a replication competent and an infective HIV virus is disclosed. When the heterologous gene is a marker gene, the spread of the virus can be observed in both in vitro and in vivo systems. The use of this vector in establishing methods for screening anti-viral compounds is also disclosed.

11 Claims, 7 Drawing Sheets

VECTOR COMPRISING A REPLICATION COMPETENT HIV-1 PROVIRUS AND A HETEROLOGOUS GENE

This is a continuation of application Ser. No. 7/249,918 filed on Sep. 27, 1988, now abandoned.

The present invention is directed to a vector comprising a replication competent HIV-I provirus and a heterologous gene, and the use of this vector. Most preferably, the heterologous gene is a marker gene that can be used to trace HIV infection.

The human immunodeficiency virus (HIV-I, also referred to as HTLV-III, LAV or HTLV-III LAV) is the etiological agent of the acquired immune deficiency syndrome (AIDS) and related disorders [Barre-Sinoussi, et al., Science 220:868–871 (1983); Gallo et al, Science 224:500–503 (1984); Levy et al., Science 225:840–842 (1984); Popovic et al., Science 224:497–500 (1984); Sarngadharan et al., Science 224:506–508 (1984); Siegal et al., N. Engl. J. Med. 305:1439–1444 (1981)]. The disease is characterized by a long asymptomatic period followed by progressive degeneration of the immune system and the central nervous system. Studies of the virus indicate that replication is highly regulated, and both latent and lytic infection of the CD4 positive helper subset of T-lymphocytes occur in tissue culture [Zagury et al., Science 231:850–853 (1986)]. The expression of the virus in infected patients also appears to be regulated as the titer of infectious virus remains low throughout the course of the disease. Molecular studies of the regulation and genomic organization of HIV-I show that it encodes at least 7 genes [Ratner et al., Nature 313:277–284 (1985); Sanchez-Pescador et al., Science 227:484–492 (1985); Muesing et al., Nature 313:450–457 (1985); Wain-Hobson et al., Cell 40:9–17 (1985)]. Three of the genes, the gag, pol and env genes are common to all retroviruses. However, the genome also encodes six additional genes that are not common to most retroviruses, the vif, tat, rev (also referred to as art and trs), 3' nef, vpr and vpu genes [Sodroski et al., Science 231:1549–1553 (1986); Arya et al., Science 229:69–73 (1985); Sodroski et al., Science 227:171–173 (1985); Sodroski et al., Nature 321:412–417 (1986); Feinberg et al., Cell 46:807–817 (1986) Wong-Staal et al, AIDS Res. and Human Retroviruses 3: 33–39 (1987); and U.S. patent application Ser. No. 193,321 filed May 12, 1988, which are all incorporated herein by reference].

Most of these genes encode products that are necessary for the viral life cycle.

The tat gene encodes a 14 kD protein that is critical for HIV replication and gene expression [U.S. patent application Ser. No. 806,263, filed Dec. 6, 1985; Rosen, C. A., et al., Nature 319:555–559 (1986); Sodroski, J. et al., Science 227:171–173 (1985); Arya et al, Science 229: supra, Sodroski, et al., Science 229, supra and Dayton, A., et al., Cell 44:941–497 (1986) which are all incorporated herein by reference]. However, mutations eliminating the ability of this gene to express a functional product can be complemented in trans in cell lines that constitutively express the tat protein.

Another gene necessary for replication is the rev gene. [U.S. patent application Ser. No. 865,151, filed May 20, 1986; Sodroski, et al., Nature 321:412–417 (1986), which are both incorporated herein by reference]. However, this gene although necessary for production of structural proteins such as the envelope protein is not necessary to produce functional regulatory proteins such as the tat gene product and the 3' nef gene product, which can be made by rev-defective proviruses.

The vif gene although not absolutely necessary encodes a 23 kD protein important for virus infectivity [Fisher, A. G., et al, Science 237: 888–893 (1987); Strebel, K., et al, Nature 328:728–730 (1987)].

The 3' nef gene, which is located at the 3' end of the viral genome immediately following the env gene and overlapping the 3' LTR, encodes a 27 kD protein which has not yet been determined to be necessary for either the infectivity or cytopathicity of the virus [Terwilliger, E., et al, J. Virol. 60:754–760 (1986); Luciw, P. A., et al, PNAS 84:1434–1438 (1987)].

Although a great deal of research has been expended on understanding this retrovirus, there have been problems with fully understanding its life cycle. As aforesaid, individuals infected with the virus typically exhibit a lengthy asymptomatic period during which viral titers are low and levels of T4+ lymphocytes are normal. This phase usually extends over a period of years. Further, the virus does not cause infection in most animals. Although chimpanzees can be infected, it is very difficult to follow the virus in chimpanzees, as they do not readily display signs of infection and very little viral protein or RNA is made.

Accordingly, it would be extremely useful to have a vector containing a replication competition HIV provirus with a heterologous gene whereby it would be possible to track the route of infection in animals and in infected tissue at a time when very little viral protein or RNA is made.

Further, it would be very useful to use such a vector in a system where the virus can be followed in vitro to screen for drugs that inhibit infection.

SUMMARY OF INVENTION

We have now discovered a vector comprising a sufficient number of nucleotides corresponding to an HIV genome to express HIV gene products necessary for viral replication and infectivity (HIV segment) and also containing a sequence of nucleotides corresponding to a heterologous gene (heterologous gene segment). This vector is sometimes referred to herein as a replication competent provirus. This vector can be used to trace the activities and functions of the virus in both in vivo and in vitro systems.

Preferably, the vector comprises an HIV segment which does not correspond to a group of non-essential nucleotide sequences from the HIV virus. Preferably, the non-essential sequences that the HIV segment does not correspond to are in the 3' end of the HIV genome, and more preferably, the HIV segment does not contain nucleotide sequences corresponding to the 3' nef sequences. Typically, the nucleotide sequences corresponding to the heterologous gene are inserted in the HIV segment where those non-essential sequences would appear. Preferably, the heterologous gene segment corresponds to a marker gene such as the chloramphenicol acetyltransferase (CAT) gene or a growth hormone such as human growth hormone (hGH).

Preferably, the vector is not more than one kilobase larger than the HIV genome, more preferably the size is no more than 900 bases larger, still more preferably it is no more than 750 bases larger, and most preferably it is no more than 700 bases larger.

BRIEF DESCRIPTION OF THE DRAWINGS

FIG. 2A shows cell counts, FIG. 2B measures reverse transcriptase activity, and FIG. 2C shows CAT activity by looking at immunoprecipitation.

FIG. 3A is an autoradiogram of a CAT assay. FIG. 3B summarizes the change in the level of CAT enzyme recorded over the course of the entire experiment.

FIG. 5A shows immunoprecipitations and FIG. 5B is a CAT assay.

DETAILED DESCRIPTION OF THE INVENTION

We have now produced a vector containing a sufficient number of nucleotides corresponding to an HIV genome to express HIV gene products necessary for viral replication and infectivity (referred to as the HIV segment) and a sequence of nucleotides corresponding to a heterologous gene (referred to as the heterologous gene segment). This vector is sometimes referred to as a replication competent provirus or provirus.

Preferably, the HIV segment corresponds to nucleotides of the HIV-1 or HIV-2 genomes. More preferably, the HIV segment corresponds to nucleotides of the HIV-1 genome. However, it preferably does not correspond to many nucleotide sequences that are not necessary for viral replication and infectivity. This is because it is preferable that the vector is no larger than one kilobase greater than the HIV genome which it corresponds to. More preferably, the size of the vector is no more than 900 nucleotide bases larger than the HIV genome. Still more preferably, the vector is no more than 750 nucleotide bases larger than the HIV genome. Even more preferably, the vector is no more than 700 nucleotide basese larger than the HIV genome. Accordingly, the non-essential nucleotides that the vector's HIV segment should correspond to can vary depending upon the size of the heterologous gene segment. Preferably, the heterologous gene segment should be about 1 kilobase or less, more preferably it should be less than about 800 nucleotides.

We have found that by using this vector the heterologous gene will follow the course of infection and replicaiton by the virus and can therefore be used as a means of identifying viral infectivity and viral function.

Figure 1:
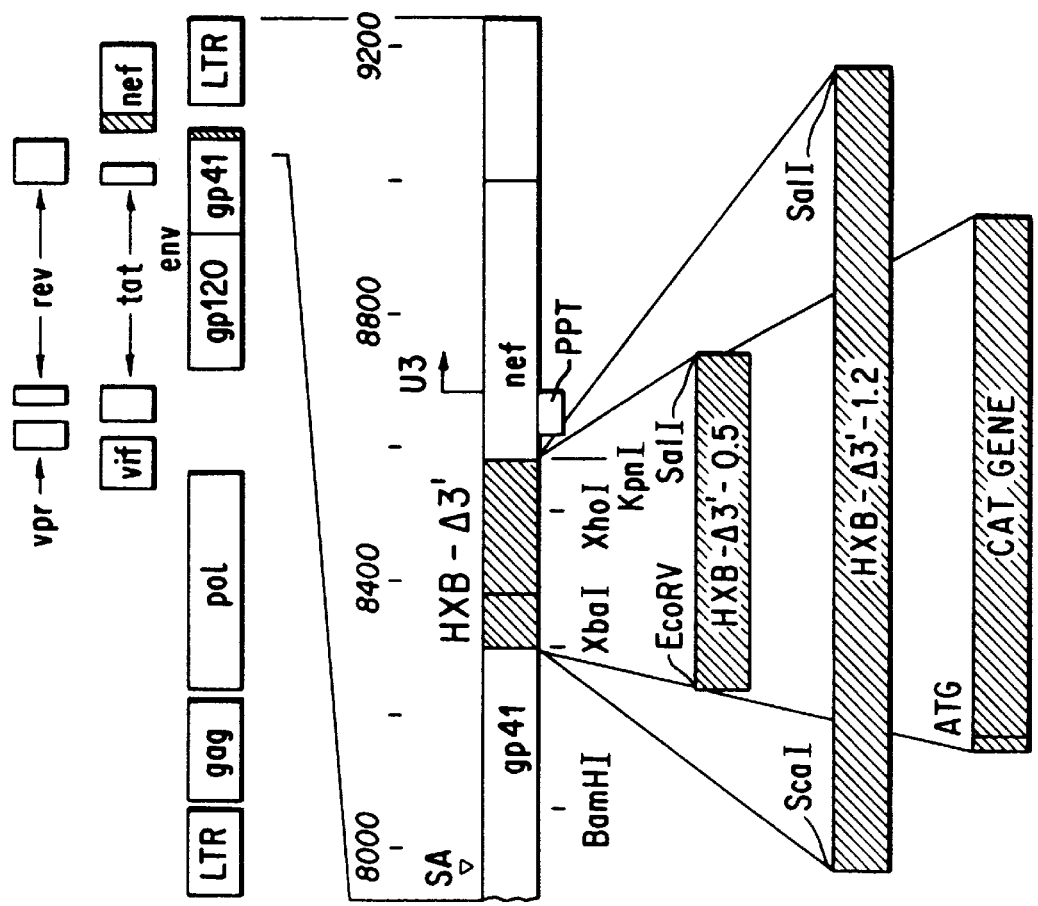
FIG. 1 is a diagram of HIV proviral constructs. The upper portion of FIG. 1 is a schematic of the parental clone pHXBc2 showing the location of the different reading frames. The lower portion of FIG. 1 is a schematic showing the 3' end of the genome and a variety of different constructs that were prepared.

The HIV segment does not correspond to a small group of non-essential nucleotide sequences from the HIV genome. Preferably, the non-essential sequences that the HIV segment does not correspond to are non-essential sequences in the 3' end of the HIV genome. More preferably, the HIV segment does not correspond to the 3' nef sequences. For example, the HIV segment does not have to correspond to the sequences in, for example, HIV-1 between the unique Xba I site and a Kpn I site located 60 nucleotides 5' to the beginning of the 3' LTR (See FIG. 1). However, there are other nucleotide sequences that the HIV segment can also not correspond to.

Any heterologous gene can be used so long as it will not disrupt the replication of the virus. More preferably, the segment corresponds to a gene whose expression can readily be traced so that it is possible to follow the replication of the virus. This would include marker genes such as the CAT gene, genes for growth hormones such as the human growth hormone gene, and many other genes well known to the person of ordinary skill in the art.

For example, by using a vector comprising an HIV segment and a CAT segment it is possible to transfect an infectious HIV virus expressing a functional CAT gene. Since CAT activity is an extremely sensitive enzyme marker this permits studies of infection by the virus that have not been possible. This result occurs because in a cell transfected with this vector, e.g. a Jurkat cell, CAT activity can be detected using as little as 10 μl of the infected culture. Accordingly, it is possible to indirectly detect viral infection at early stages where the synthesis of viral products is occurring at extremely low levels that are difficult to directly measure by looking for the presence of the marker. Use of such a vector permits rapid analysis of tissues that are infected by the viral segment as well as measurement of the level of virus expression in different organs. This vector is also useful in studies of superinfection, as well as following the course of virus infection in vivo and in vitro.

The heterologous segment can be inserted anywhere in the vector so long as it does not disrupt a reading frame which expresses a necessary viral function. Preferably, the heterologous gene segment is inserted in the vector in the portion of the HIV segment wherein the non-essential sequences would have appeared, for example, the 3' nef sequence. However, this is not necessary and the heterologous gene segment can be inserted in numerous other reading frames in the vector besides where the 3' nef sequence would appear. For example, it is possible to cause a deletion in the 3' nef sequence to reduce the size of the HIV segment and insert the gene elsewhere in the HIV segment. The only caution that must be taken in preparing the vector is that sequences necessary for viral replication are not disrupted by the deletion or the insertion. However, this can readily be determined by empirical tests.

In preparing a vector according to the present invention many techniques are possible. For example, one can use a proviral genome for the HIV segment and foreign DNA segments for the heterologous gene segment or one can chemically synthesize the HIV and heterologous gene segments. Other techniques known to the skilled artisan based upon the present disclosure can also be used to prepare the vector.

In one method one can use a plasmid containing an infectious HIV proviral clone, delete a non-essential sequence, for example, the 3' nef sequence and insert a DNA segment for a heterologous gene in the deleted region to produce a vector according to the present invention. For example, an infectious proviral clone derived from pHXBc2 [Fisher, A. G., et al., Nature 316:262–265 (1985)] which contains an artificially introduced restriction enzyme cleavage site near the 3' end of the gene encoding the envelope transmembrane protein [Lobel, L. I., PNAS 81:4149–4153 (1984)] and referred to as pHXBc2-Xba I can be used, although any replication competent HIV proviral plasmid can be used therefore. This mutation introduced a unique Xba I site, as well as a termination signal at a position 17 codons before the natural termination signal of the envelope glycoprotein (see FIG. 1). The presence of this linker insertion did not alter the kinetics of virus replication as compared to the pHXBc2 parent.

Sequences in this provirus between the unique XbaI site and a Kpn I site located 60 nucleotides 5' to the beginning of the 3' LTR were removed, resulting in a mutant provirus (pHXB-Δ3'), which contains a deletion of 280 nucleotides including the 3' end of the env gene, the 3' nef initiation codon and 220 nucleotides of the 3' nef gene. Mutant proviruses equivalent to this one can readily be constructed by the person of ordinary skill in the art by using standard techniques. Typically, one uses known restriction enzyme sites to delete and/or insert the various sequences. Although the 3' nef coding sequences extend beyond the Kpn I site in the 3' direction, it is preferable not to remove them because removal of additional nucleotides can disrupt the 3' LTR.

Thereafter, one inserts a heterologous gene segment into the HIV segment wherein this heterologous gene segment corresponds to a sufficient number of nucleotides of the desired heterologous gene to express a functional product. This segment preferably contains the initiation and termination signals as well as the nucleotide sequences for the desired gene. Preferably, the heterologous gene segment is about 1200 nucleotides or less, more preferably, about 1000 nucleotides or less, and still more preferably, about 800 nucleotides or less.

Preferably, one would use a heterologous gene that can be used as a marker. For example, the CAT gene corresponding to a gene that is less than about 800 nucleotides. The entire coding sequence for this gene is located within a 750 nucleotide-long region. Furthermore, a simple sensitive assay for this enzyme activity is exists [Gorman, C. M., et al., *Mol. & Cell. Biol.* 2:1044–1051 (1982)] and antisera that recognizes the CAT protein is also readily available [Gorman, C. M. et al., *Cell* 42:519–526 (1985)].

Proviral plasmids incorporating a nucleotide sequence corresponding to the CAT gene can readily be made by inserting the nucleotide sequence between restriction enzyme cleavage sties, for example, the Xba I and Kpn I sites, using standard techniques. Other sites can also be used such for insertion of the heterologous gene segment, for example the Xba I site and the Xho I site within the 3' nef gene.

The vector is then used to transfect a desired cell by standard techniques. For example, one can transfect a cell in vitro using, for example, the calcium phosphate coprecipitation technique. Alternatively, this vector can be used to transfect living cell in vivo.

After transfection of the cells, either in vitro or in vivo, one would use standard techniques to detect the presence of the marker gene. For example, in the above-described instances where the vector contains a CAT gene, one merely measures for CAT activity. This technique would permit in vivo screening of the spread of the virus in various tissues. By determining which tissues show CAT activity, one can learn how the virus spreads. Additionally, one can also measure the quantity of CAT activity and thus determine the level of the virus in the various tissues.

Using this vector to transfect cells in vitro can permit a very rapid system for screening drugs. With a sensitive marker like CAT, it is possible to detect the expression of the marker about one day after the cells have been transformed. Thus, using this vector, one can rapidly screen for drugs that affect the spread of the virus in infected cells and also for compounds that will affect the ability of the virus to infect a cell. For example, one can add a predetermined compound to a cell culture and thereafter try to transfect those cells with the vector of the present invention. Thereafter, one can measure the level of the marker in the cell to determine the effectiveness of a compound in preventing the spread of the virus. Alternatively, one can tranfect cells with the vector of the present invention, measure the level of activity of the marker and then add the predetermined compound to the cells. One then measures the activity of the marker to determine the effectiveness of the compound.

By measuring the level of activity of the marker it is possible to determine, not only the effectiveness of the predetermined compound against the virus, but the degree of effectiveness of this compound. Controls can be run simultaneously or shortly after these test are run.

Compounds that appear to show an effect against the virus in vitro can then be administered by standard techniques to one of the above-described in vivo systems to test the effectiveness of this compound in vivo.

The present invention is further illustrated by the following examples. These examples are provided as an aid to understanding the invention and are not to be construed as a limitation thereof.

EXAMPLES

Cell Lines and Viruses

The HIV proviral clone pHXBc2, as described in Fisher, A. G., et al., *Nature* 316:262–265 (1985) was used. The Jurkat cell line is a T4+ human malignant T-lymphoblastic line provided by the lab of Cox Terhorst. The cells were maintained at 37° C. in a $CO_2$ incubator in RPM1 1640 medium supplemented with 10% of fetal bovine serum, glutamine, penicillin (1,000/ML) and streptomycin (100 µg/ml). C8166 cells are an HTLV-1-transformed human lymphocyte line expressing very high levels of the T4 marker as described in Salahuddin, S. Z., et al., *Virology* 129:51–64. The cells express no known products of HTLV-I except the tat protein. Cells were maintained under the same conditions as the Jurkat line. HeLa cells, a human cervical carcinoma line, were maintained under similar conditions except the medium used was Dulbecco's Modified Eagles Medium (DME) supplemented with 10% fetal bovine serum.

DNA Transfections

Jurkat cells were pelleted for 5 minutes at 1000 rpm, washed once with serum-free RPM1 medium, and then resuspended in fresh RPM1 medium at a density of $10^7$ cells/ml. One ml of cells were then added per transfection to tubes already containing the plasmid DNA in 2 ml of serum-free RPM1 plus 150λ of a 5 mg/ml stock solution of DEAE dextran in 1M Tris-Cl pH 7.3. Tubes were then incubated at 37° C. for one hour with occasional agitation. The cells were then pelleted, washed once with 10 ml of serum-free RPM1, and resuspended in 15 ml of RPM1 plus 15% fetal bovine serum. All cells were subsequently given a complete medium change daily, throughout the course of the experiment.

HeLa cells were seeded at a density of $10^6$ cells/100 mm plate the day before transfection. Transfection mixes contained the DNA in 1 ml of Hepes Transfection Buffer plus 0.11 ml of 1.25 $CaCl_2$ added disguise with agitation. Transfection mixes were incubated for 30 minutes at room temperature, then added dropwise to the medium over the HeLa cells.

Cells were then incubated for 24 hours. Afterwards the medium was removed and the cells were washed once with 7 ml of serum-free medium. The cells were then shocked by treatment with 2 ml of 10% DMSO. After 10 minutes the DMSO was aspirated and 10 ml of fresh medium were added to the plates. Cells were collected for assay 48 hours later.

Cat Assays

Cells were spun down, washed once with Phosphate Buffered Saline (PBS), and freeze/thawed three times in a small volume of 200 mM Tris, pH 7.5. Lysates were then analyzed for CAT activity in a standard assay mix containing $^{14}$C-chloramphenicol and Acetyl CoA as described in Sodroski, J. G., et al., *Science* 225:381–385 (1984). Percent conversion of chloramphenicol to the acetylated forms was determined by ascending thin-layer chromatography and liquid scintillation counting of the spots cut from the plate.

Reverse Transcriptase (RT) Assays

For each assay, 1 ml of culture medium from each sample was collected and centrifuged for one hour at 15,000×g to pellet virions. Pellets were resuspended in 10 μl of 50 mM Tris HCl pH 7.5, 1 mM dithiothreitol, 0.25 M KCl, and 20% glycerol. RT activity was assayed in 50λ reaction mixes using oligo(dt)-poly (A) template-primer and magnesium cofactor, as described in Rho H. M., et al., *Virology* 112: 355–360 (1981).

HIV p24 Assay 1 ml of culture medium from each well was collected and centrifuged for 1 hour at 15,000×g to pellet virions. Pellets were resuspended in 100 μl of assay buffer containing 0.5% Triton X-100, and assayed using a commercially prepared HIV p24 radioimmune assay kit (Lee, T. H., et al., *Proc. Natl. Acad. Sci. USA*. 81:3856–3860 (1984) according to manufacturers directions. Standards supplied with the kit were used to quantitate protein levels in the samples.

Immunoprecipitation

Cells were spun down, washed once with PBS, and resuspended in 2.5 ml of cysteine-free RPM1 plus 10% fetal bovine serum supplemented with 50 μci/ml of $^{35}$S-cysteine. Cells were labelled overnight, then harvested, washed once with PBS, and lysed in 0.5 ml of 0.05 M tris, HCl pH 7.0, 0.15M NaCl, containing 1% Triton X-100, 1% sodium deoxycholate, and 0.1% SDS. Immunoprecipiation with AIDs patient antiserum and polyacrylamide gel electrophoresis were performed described in Lee, T. H., et al., *PNAS* 81, supra.

Preparation of a Vector

We used plasmid pHXBc2-Xba I, an infectious proviral clone derived from pHXBc2 [Fisher, A.G. et al, *Nature* 316, supra (1985)] which contains an artificially introduced restriction enzyme cleavage site near the 3' end of the gene encoding the envelope transmembrane protein [Lobel, L. I., *PNAS* 81:4149–4153. This mutation introduced a unique Xba I site, as well as a termination signal at a position 17 codons before the natural termination signal of the envelope glycoprotein (See FIG. 1). The presence of this linker insertion did not alter the kinetics of virus replication as compared to the pHXBc2 parent.

Thereafter, sequences in this provirus between the unique XbaI site and a Kpn I site located 60 nucleotides 5' to the beginning of the 3' LTR were removed, resulting in a mutant provirus (pHXB-Δ3'), which contains a deletion of 280 nucleotides including the 3' end of the env gene, the 3' nef initiation codon and 220 nucleotides of the 3' nef gene. Although the 3' nef coding sequences extend beyond the Kpn I site in the 3' direction, it is preferable not to remove them because removal of additional nucleotides can disrupt the 3' LTR.

A heterologous gene segment was then inserted. This segment preferably contains the initiation and termination signals as well as the nucleotide sequences for the desired gene. As shown, in FIG. 1 two DNA segments derived from the plasmid pBR322 were inserted in place of the deleted segment to produce the plasmids pHXB-Δ3'-0.5 and pHXB-Δ3'-1.2. pHXB-Δ3' was constructed by deleting the region between a 12 base pair Xba I linker insertion into the 3' end of the env gene and a Kpn I site located within the 3' nef gene. pHXB-Δ3'-0.5 and pHXB-Δ3'-1.2 contain segments of pBR DNA inserted in place of the region deleted in pHXB-Δ3'. The segment inserted in pHXB-Δ3'-0.5 was derived from the 470 base pair pBR fragment located between the unique EcoR I and Sal I cleavage in that plasmid. The segment in pHXB-Δ3'-1.2 was derived from a 1.17 kb fragment excised using the Sal I and Sca I sites. These proviral clones were then transfected into Jurkat cells and monitored daily for signs of HIV infection using the technique described above. Parameters checked included cell number, synctia formation and reverse transcriptase activity of the culture supernatants. See Table 1.

Cells transfected as described above by pHXBc2-Xba I, which contained a 280 nucleotide deletion of the env and 3' nef sequence as described above, replicated as well as that produced by the wild type provirus. Cells transfected with pHXB-Δ3'-0.5, which in addition contained a 475 nucleotide insertion for a net increase of 190 nucleotides also produced virus that replicated as well as the wild type. Cells transfected with pHXB-Δ3'-1.2, which contained an insert of 1.17 kilobases for a net increase of about 890 base pair, produced virus which were much attenuated especially in initial replication. Transfection with this plasmid resulted in an initial appearance of only small numbers of synctia and very low levels of reverse transcriptase activity. Only at later times post-transfection (days 10–12) was there some increase in the number of synctia and the amount of reverse transcriptase activity in the pHXB-Δ3'-1.2-transfected culture coincident with a decline in the number of viable cells.

Filtered supernatant collected from the pHXB-Δ3'-1.2-transfected culture at this time proved unable to initiate new cycles of infection when added to fresh uninfected Jurkat cells. Supernatants containing 1000–2000 units of reverse transcriptase activity from cultures transfected with either wild type pHXBc2, pHXB-Δ3', or pHXB-Δ3'-0.5 plasmids were capable of initiating new rounds of infection in fresh Jurkat cells.

A vector was then constructed using the gene for chloramphenicol acetyltransferase (CAT). This gene is available to the skilled artisan. The entire coding sequence for this gene is located within a 750 nucleotide-long region. Moreover, a simple sensitive assay for its enzyme activity exists (Gorman, C. M., et al., *Mol. and Cell. Biol.* 2: 1044–1051 (1982)) and antisera that recognize the CAT protein are available (Gorman, C. M., et al., *Cell* 42:519–526 (1985).

Two vectors incorporating the coding sequences for the CAT gene were made. A segment of DNA approximately 800 nucleotides long that contained the entire coding sequence for the CAT gene as well as the translation initiation and termination signals was inserted into each provirus. For pHXB-CAT1 the CAT gene was inserted between the Xba I and Kpn I sites in place of the sequences removed in the deleted provirus pHXB-Δ3' (See FIG. 1). For pHXB-CAT2 a similar insertion was made between the Xba I site and the Xho I site that is located within the 5' end of the 3' nef gene. In both constructions the CAT gene is located downstream from the natural splice acceptor used for production of the 3' nef protein (Muesing, M. A., et al., *Nature* 313:450–458 (1985). The plasmid pHXB-CAT1 has a net size increase of 570 bp over the wild type pHXBc2 proviral clone and in turn is 110 bp smaller than pHXB-CAT2. Both vectors were transfected into Jurkat cells by the transfection technique described above, which were monitored daily thereafter for signs of HIV infection.

FIG. 2 shows that the virus produced by the pHXB-CAT1 vector replicated almost as well as the wild-type virus.

Figure 2A:
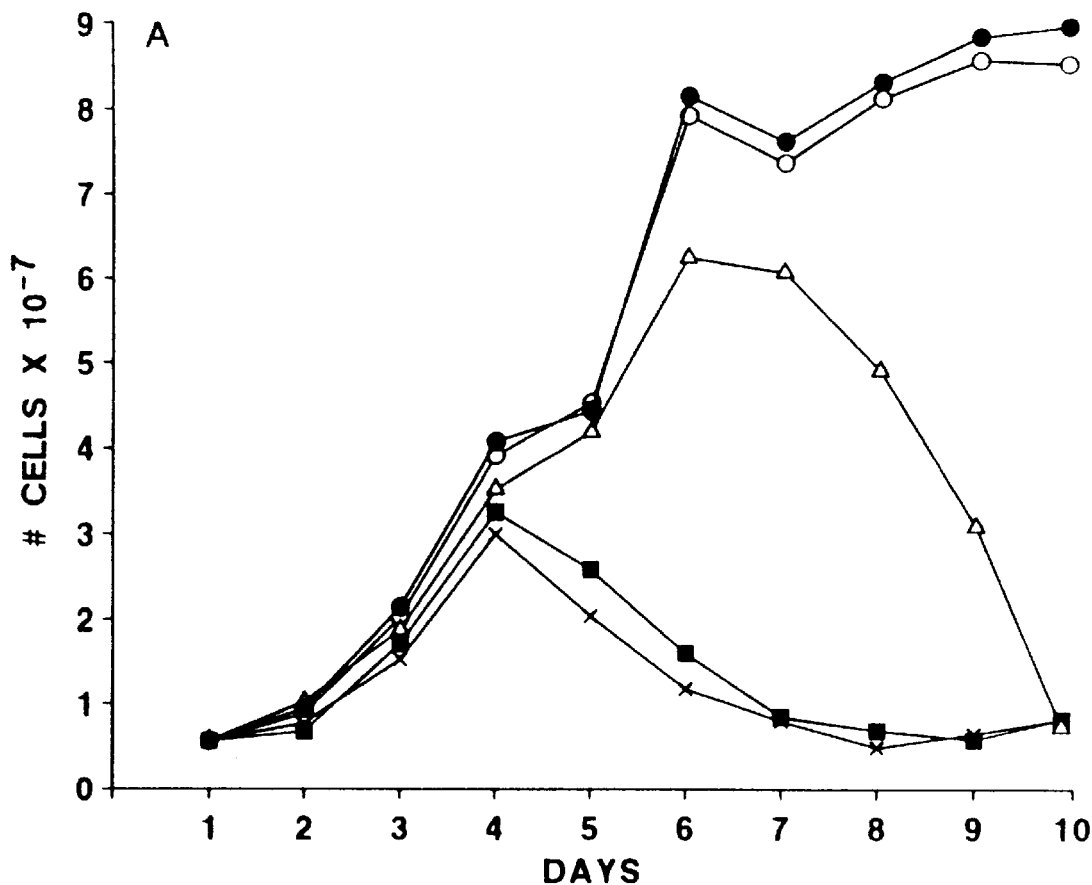
FIGS. 2A–C shows the kinetics of replication of viruses produced by different vectors containing the CAT gene as the heterologous segment CAT gene inserts.
Figure 2B:
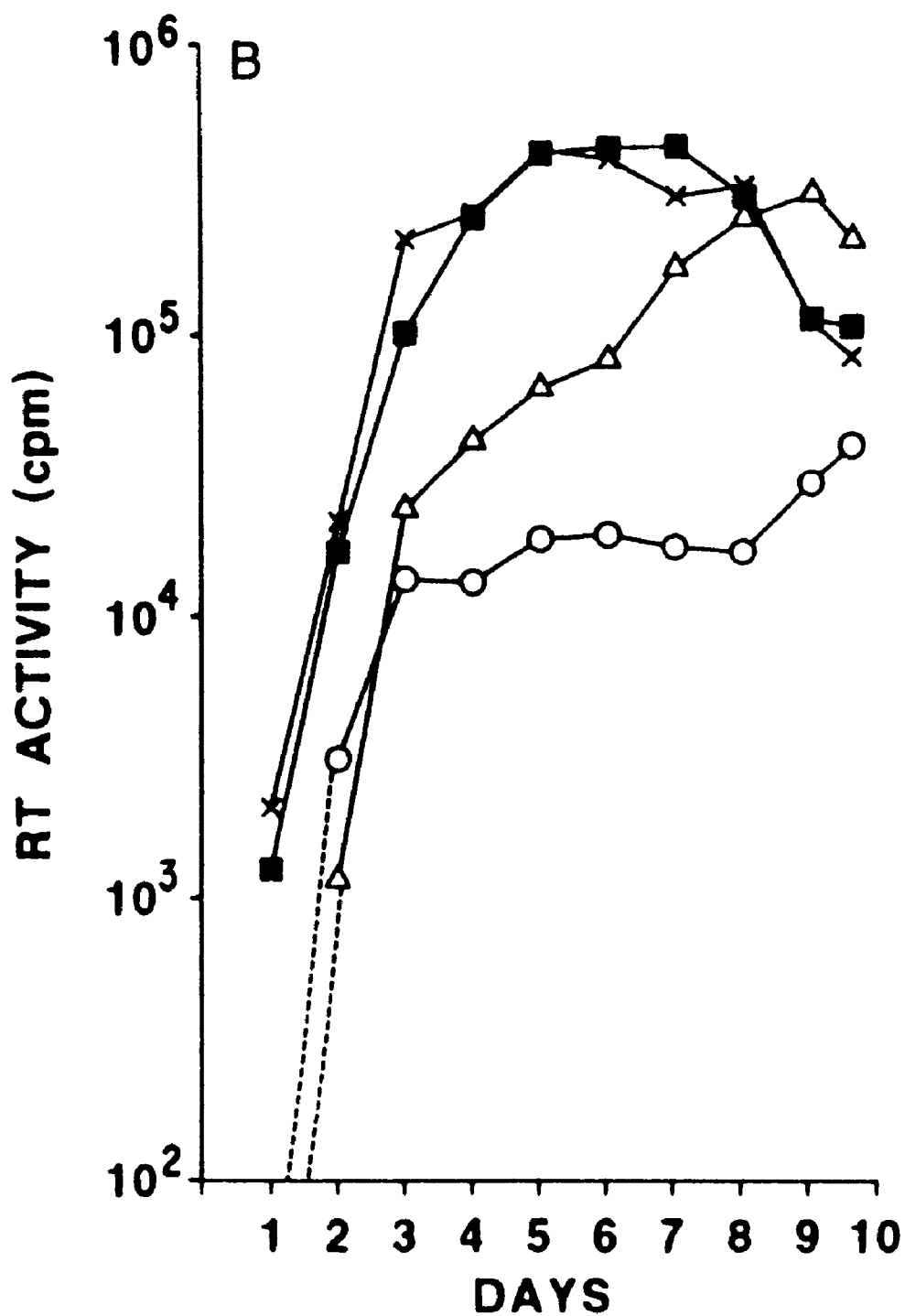
Figure 2C:
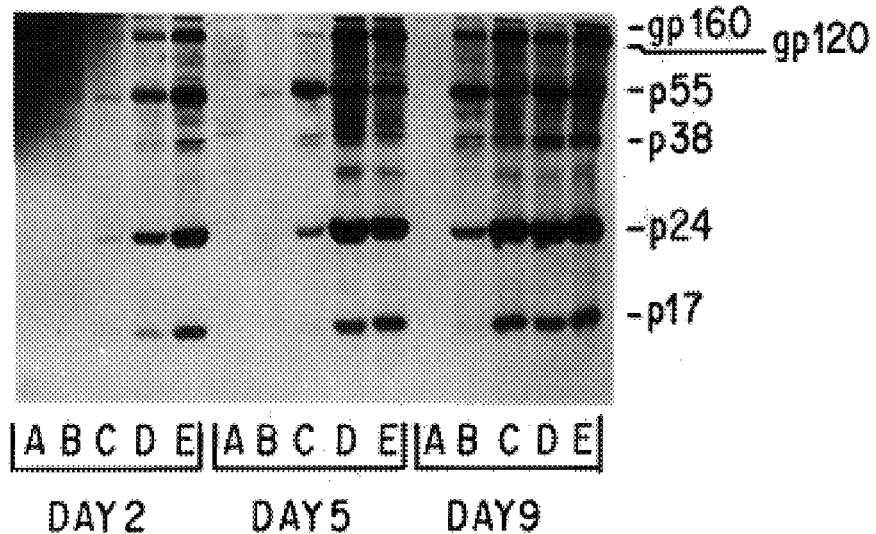

Jurkat cells were transfected on day 0 with over 10 micrograms of one of the proviral clones. The cells were monitored daily thereafter for signs of virus activity. Duplicate cultures were transfected with each plasmid to insure sufficient cells would be available for sampling. Media on the cells were changed daily and one-half of the cells from each culture was removed on day four to keep the cells for a longer time in log phase growth. FIG. 2A shows cell counts and uses the following symbols: ●-mock transfection; ○-pHXB-CAT2; Δ-pHXBCAT1; ■-pHXB-Δ3; and X-pHXBc2. FIG. 2B shows the reverse transcriptase activity where the symbols have the same meaning as above. Immunoprecipitation of protein is shown in FIG. 2C. 5 ml aliquots of each culture were collected 2, 5 and 9 days after transfection and labelled overnight with $^{35}$S-cysteine by standard techniques. Samples were then collected, detergent lysed and immunoprecipitated with AIDS patient antiserum using standard techniques. Lane A-mock transfection, Lane B-pHXB-CAT2, Lane C-pHXB-CAT1, Lane D-pHXB-v3' and Lane E-pHXBc2.

The course of infection in cells transfected with pHXB-CAT1 appeared to lag behind that in the culture transfected with pHXBc2 by about 2–3 days, by whatever parameter was measured. However, by day 8–9 post-transfection the pHXB-CAT1 culture attained high levels of reverse transcriptase activity and dramatic cytopathic effect very similar to what was seen in the wild type culture. By contrast, although the culture transfected with pHXB-CAT2 exhibited low levels of reverse transcriptase activity from three days-post-transfection onward and displayed significant syncytia formation, the infection did not progress normally and significant cytopathic effect was not observed as late as ten days post-transfection. Furthermore, filtered supernatant fluid taken from the culture transfected with pHXB-CAT2 at day ten did not produce indications of virus infection when applied to fresh Jurkat cells. Corresponding supernatants from cultures transfected with pHXBc2, pHXB-Δ3', and pHXB-CAT1 all initiated new cycles of infection when cultivated with fresh cells, even when first diluted to compensate for differences in RT levels between the samples (data not shown).

These observations are closely mirrored by the results of protein-labelling experiments described in FIG. 2C. HIV proteins are strongly evident in labelled aliquots from cultures transfected with either the wild-type or pHXB-Δ3' constructs even when labelling was initiated only 48 hours post-transfection. The small difference seen in this particular experiment between the day 2 pHXB-Δ3' and pHXBc2 lanes was not repeatable. Virus-specific proteins are only weakly evident in lanes representing day 2 lysates from cells transfected with pHXB-CAT1 or pHXB-CAT2. However, by day 5 the virus-specific bands are stronger in the lysate from the pHXB-CAT1 culture and by day 9 the pHXB-CAT1 lane is virtually indistinguishable from the pHXBc2 and pHXB-Δ3' lanes. By contrast, the day 5 lysate from the culture transfected with pHXB-CAT2 is not significantly different from the day 2 lysate. Only in the day 9 lysate can an increase in the intensity of the virus-specific bands in the pHXB-CAT2 culture be seen. Still at this time the amounts of viral proteins detected are well below those observed in the lysates from the other transfected cultures.

Figure 3A:
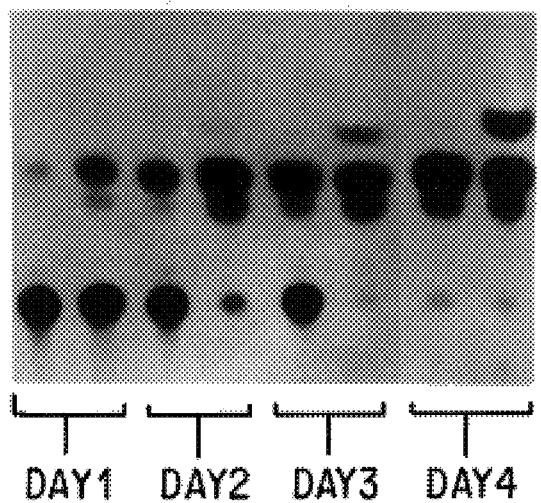
FIGS. 3A–B shows CAT activity in cultures transfected with the vector pHXB-CAT1.
Figure 3B:
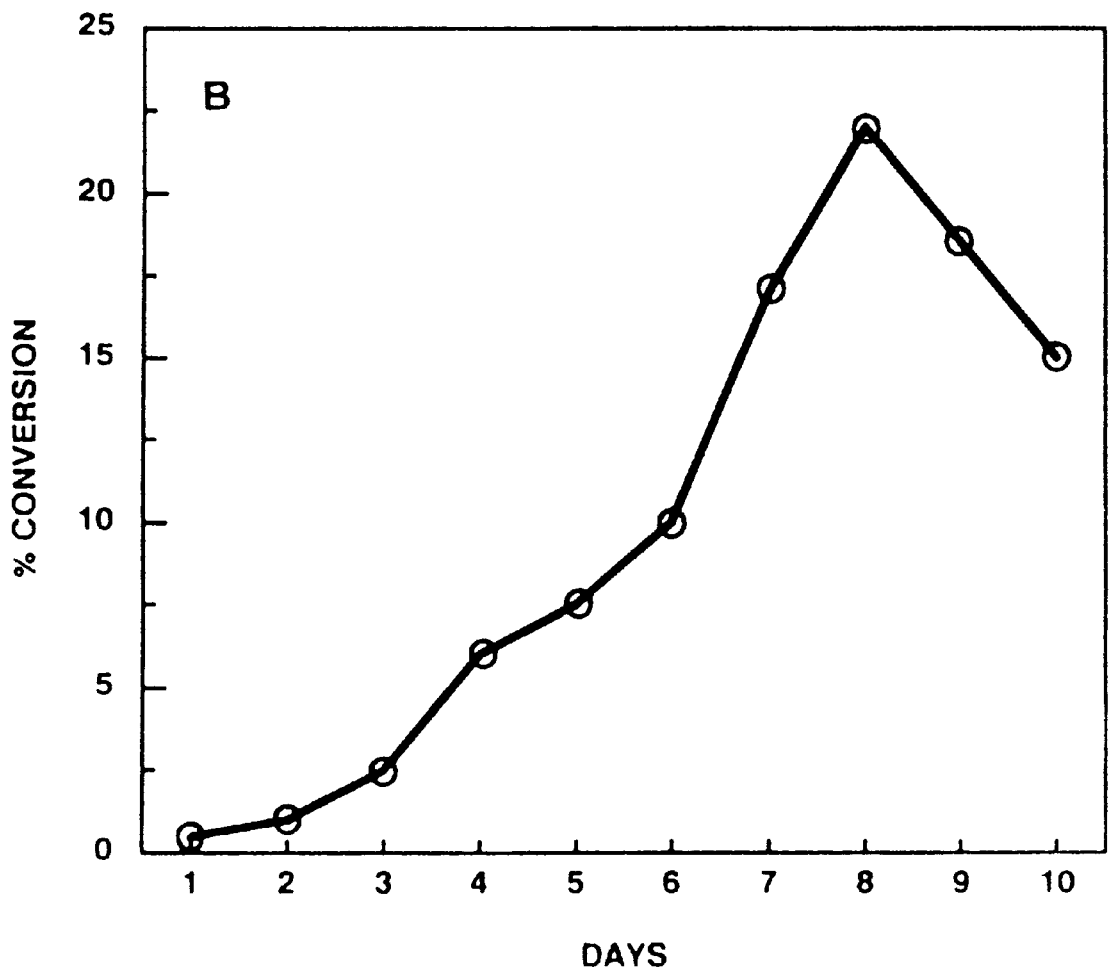

To test for expression of the inserted CAT gene, aliquots of Jurkat cells transfected with pHXB-CAT1 were collected daily. Results of CAT assays for these samples are summarized in FIGS. 3A and 3B. 1 ml from the culture was collected daily. The cells were washed once with PBS and then resuspended in 150 μl of 200 mM Tris at pH 7.5 for CAT assays. FIG. 3A is an actual autoradiogram of a CAT assay and represents conversions obtained using extract from Day 1 through Day 4 in the experiment. Each pair of spots in the autoradiogram represents conversion after 5 and 60 minute reaction times. The extracts from Day 3 post-transfection onward had to be assayed at 10 or 100-fold dilutions to maintain the conversion within the linear range of the assay. FIG. 3B summarizes the change in the level of CAT enzyme activity recorded over the entire course of the experiment. The scale used for the graph is percent conversion of $^{14}$C-chloramphenicol per minute by $^{70}$ μl of 1×10 dilution of the original samples.

CAT activity was easily detectable only one day post-transfection and quickly progressed to very high levels as the infection spread through the culture. The slight decline in the level of CAT expression at late times post-transfection presumably reflects the drastic loss in viability of the culture which was occurring by this time.

Expression of the gag/pol and envelope proteins of HIV is known to require the presence of the rev gene product. Evidence also exists which suggests that the 3' nef gene product is made independently of rev. The mRNA for the 3' nef product splices out the known positive and negative cis-acting elements crucial to rev regulation. To test whether expression of CAT enzyme by pHXB-CAT1 is under rev control, we introduced a frame shift at the Bam HI site that eliminated the ability of the viral segment to produce a functional rev protein. The pHXB-CAT-1 and pHXB/BFS-CAT1 plasmids were then co-transfected into plates containig $10^6$ HeLa cells with or without a rev expressor plasmid (pIIIexart) by the transfection method described above. HeLa cells, which do not express T4, were used so that re-infection of cells by the nondefective pHXB-CAT1-derived virus would not occur. See FIG. 4. 10 μg of each proviral plasmid was used, plus 8 μg of pIIIexart. Forty-eight hours post-transfection the cells were scraped into PBS, spun down, and resuspended in 150 μl of 0.25 M Tris Cl pH 7.5 for CAT assays. The autoradiogram shows percent conversions obtained after 5 minutes (first lane of each pair) and 60 minutes (second lane of each pari) incubations using 70 μl of each lysate. Control lysate was from transfection of a construction otherwise identical to pHXB-CAT1 in which the CAT gene was inserted in the reverse orientation (pHXB-CAT-anti).

Figure 4:
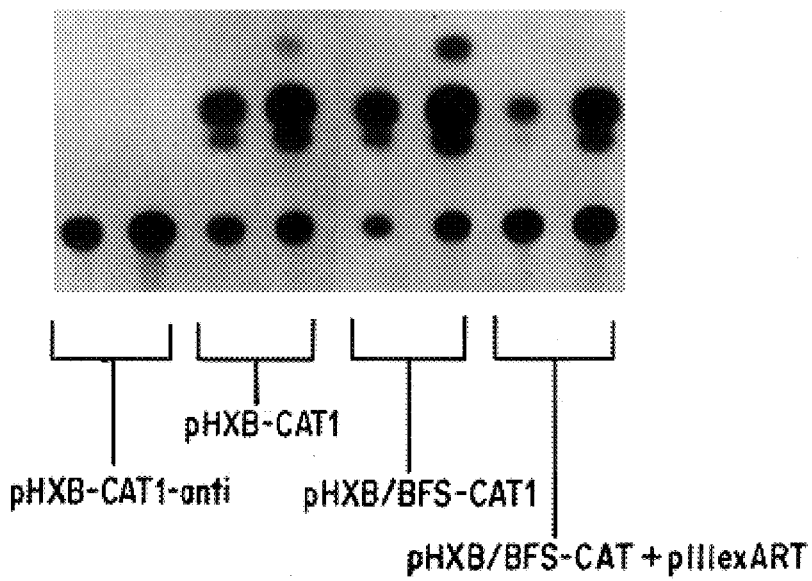
FIG. 4 illustrates autoradiograms of cells transfected with either the vector pHXB-CAT1 or a rev-defective variant pHXB/BFS-CAT1 either with or without a rev expressor.

As shown in FIG. 4, CAT activity in cells transfected with pHXB/BFS-CAT1 was similar to that seen in cells transfected with pHXB-CAT1. Co-transfection of HXB/BFS-CAT1 with a rev expressor plasmid, pIIIexart, resulted in about a 4-fold decrease in CAT activity. This is consistent with a reported decrease in the ratio of spliced to unspliced HIV mRNAs seen in the HIV mRNAs seen in the presence of rev. Therefore, expression of CAT in pHXB-CAT1 is not dependent on the presence of the HIV rev protein.

An assay for screening anti-viral drugs using the pHXB-CAT1 vector was performed. Duplicate sets of C8166 cell cultures were infected with equivalent titers of virus stocks derived from either pHXBc2 or pHXB-CAT1. Different concentrations of either azidothymidine (AZT) [Mitsuya, H., et al, *PNAS* 82:7096–7100 (1985)], 2'3'-dideoxycytosine (ddC) [Mitsuya, H., et al, AIDS: Modern Concepts and Therapeutic Challenges pp. 303–333 (New York: Marcel Dekker) (1987)] or 2'3'-dideoxy-adenosine (ddA) [Mitsuya, H. et al, AIDS: supra]; three drugs known to inhibit HIV replicaiton, were added to the infected cultures. Cultures with no drug served as controls. As shown in FIG. 5, the marked decreases in viral protein expression observed in the presence of optimal doses of the different drugs correlates closely with changes in the level of CAT enzyme measured. The C8166 cells were set up in 24-well plates at a density of 2×10⁵ cells/ml, 1 ml per well, in varying concentrations of drug or with no drug. Duplicate wells were set up for each drug concentration. 2,000 RT units of wild type pHXBc2-derived virus or 2,000 RT units of pHXB-CAT1-derived virus were added to each well. RT activity in the virus stocks was determined as described above. Cells were then incubated for 1 week with a partial medium change on Day 4. Aliquots of the cells and media were collected and assayed on Day 7.

Figure 5A:
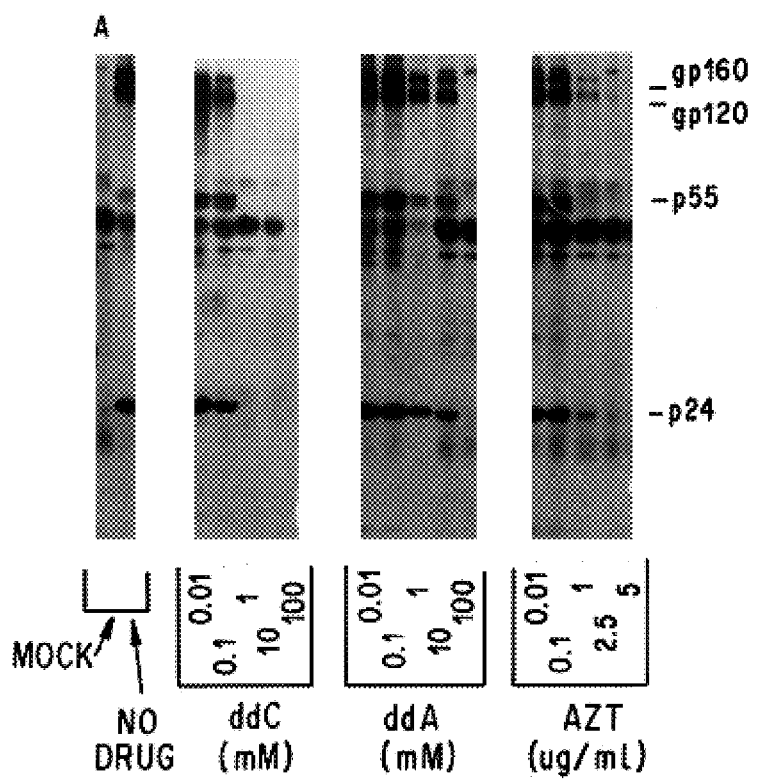
FIGS. 5A–B shows inhibition of virus replication in cultures infected with pHXBc-2 and pHXB-CAT1-derived viruses by AZT, ddC or ddA.

FIG. 5A shows protein immunoprecipitations. Cells in wells infected with pHXBc2-derived virus were labelled overnight with $^{35}$S-cysteine. Samples were then collected, detergent lysed, and immunoprecipitated with AIDS patient antiserum.

Figure 5B:
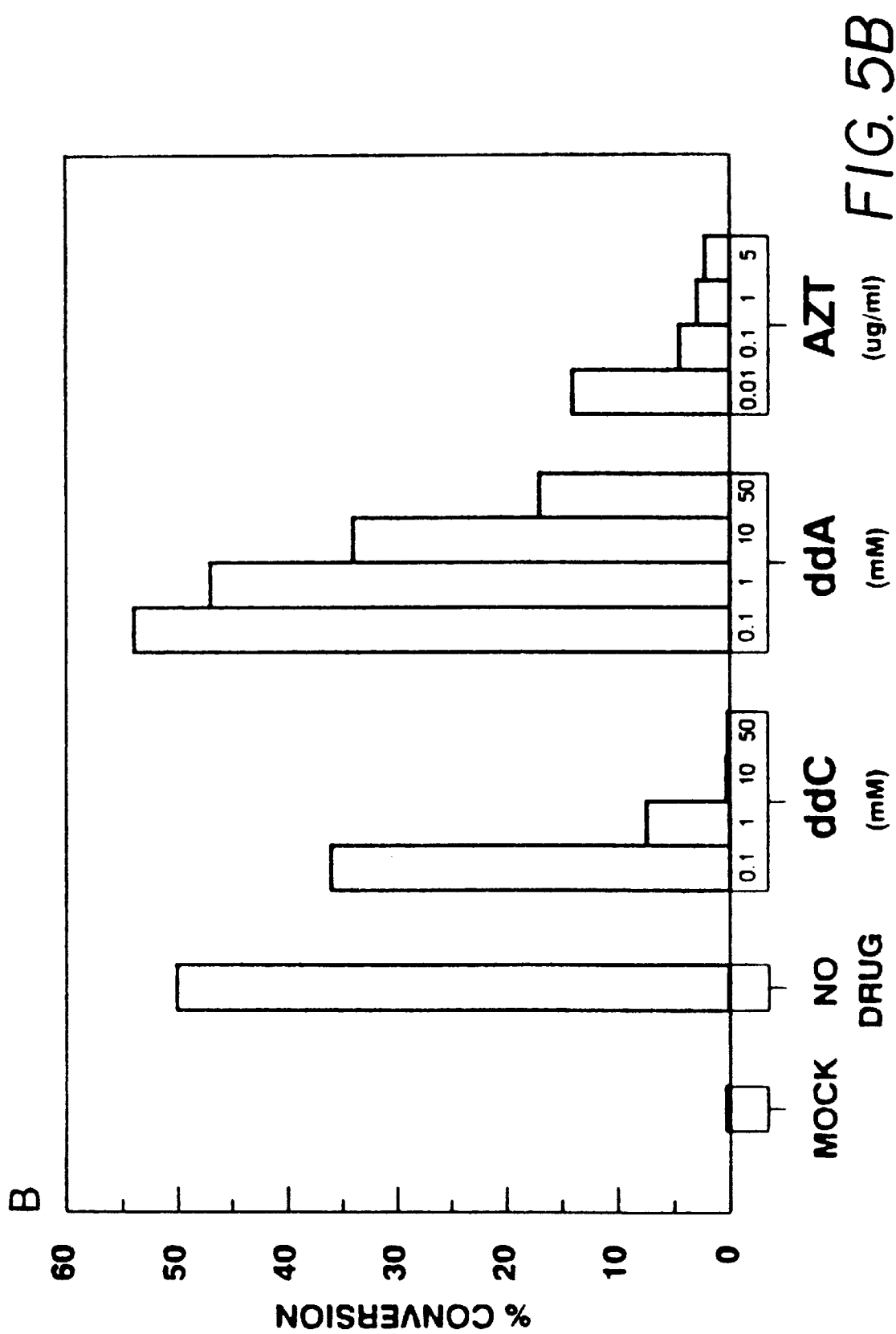

FIG. 5B shows the results of CAT assays. Cells in wells infected with pHXB-CAT1-derived virus were washed and collected in 85μl of 0.25 M Tris Cl pH 7.5. The scale used in the graph represents percent conversion of $^{14}$C-chloramphenicol in 60 minutes by 70 μl of each extract.

The experiment was repeated using an equal mixture, as determined by measurement of cell-free reverse transcriptase activity, of the pHXBc2 and pHXB-CAT1 virus preparations. Under these conditions the presence of the replicating wild type virus did not inhibit the production of CAT enzyme by the pHXB-CAT1-derived virus. After one week the levels of CAT enzyme in cultures treated with increasing concentrations of AZT correlated closely with the total amounts of viral protein present in the cultures (data not shown).

The results demonstrate that a foreign gene can be incorporated into an HIV vector and be successfully expressed without disrupting functions critical for virus replication and cytopathic effect. The major constraint appears to be size. The normal full-length HIV is apparently close to the maximum size permitted for efficient transmission, as proviruses with net size increases of 700 nucleotides or more compared to the wild type were unable to mount as successful infections following exposure of T-cells to supernatants from cells transfected with these plasmids. The results also show that the HIV-CAT1 virus can be used to measure the effect of anti-viral drugs. Use of this virus should permit a rapid, quantitative means of anti-viral drug activity. The results also show that a gene in the position of 3' nef can be expressed with absence of rev activity.

The mutations in pHXB-Δ3' introduces a premature termination codon into the env gene without appending additional amino acids. We conclude that the C-terminal 17 amino acids of the gp41 envelope glycoprotein are not required for normal replication and cytopathic activity of HIV in T-cells in culture.

It is evident that those skilled in the art, given the benefit of the foregoing disclosure, may make numerous other uses and modifications thereof and departures from the specific embodiments described herein without departing from the inventive concepts, and the present invention is to be limited solely by the scope and spirit of the appended claims.

TABLE 1

| PLASMID | SYNCITIA FORMATION | | CYTOPATHIC EFFECT | | REVERSE TRANSCRIPTASE | | CELL-FREE TRANSMISSION |
| --- | --- | --- | --- | --- | --- | --- | --- |
| | DAY 5 | DAY 12 | DAY 5 | DAY 12 | DAY 5 | DAY 12 | (2000 RT units) |
| pHXBc2 | +++ | + | ++ | +++ | +++ | +++ | YES |
| pHXB-Δ3' | +++ | + | ++ | +++ | +++ | +++ | YES |
| pHXB-Δ3'-0.5 | +++ | + | ++ | +++ | +++ | +++ | YES |
| pHXB-Δ3'-1.2 | + | ++ | − | ++ | + | ++ | NO |

We claim:

1. A vector comprising:
   (a) a sufficient number of nucleotides corresponding to an HIV genome to express HIV gene products necessary for viral replication and infectivity (the HIV segment); and inserted in the HIV segment (i) in a region of non-essential HIV nucleotide sequences or (ii) instead of a region of non-essential HIV nucleotide sequences
   (b) a sufficient number of nucleotides corresponding to a heterologous gene to express a functional protein (the heterologous gene segment).

2. The vector of claim 1, wherein the heterologous gene segment corresponds to a marker gene.

3. The method of claim 2, wherein the HIV segment corresponds to nucleotides of the HIV-1 or HIV-2 genomes.

4. The vector of claim 3, wherein the HIV segment corresponds to nucleotides of the HIV-1 genome.

5. The vector of claim 2, wherein the marker gene is a chloramphenicol acetyltransferase gene or a growth hormone gene.

6. The vector of claim 2, wherein the size of the total vector is less than about 900 nucleotide bases greater than the size of the HIV-1 or HIV-2 genome.

7. The vector of claim 2, wherein the total size of the vector is no more than about 520 nucleotide bases longer than the HIV genome.

8. The vector of claim 2, wherein the vector is no more than about 700 nucleotide bases longer than the HIV-1 or HIV-2 genome.

9. The vector of claim 2, wherein the heterologous gene segment is inserted in the HIV segment instead of the region of non-essential HIV nucleotide sequences wherein the non-essential nucleotide sequences are in the 3' end of the HIV genome.

10. The vector of claim 2, wherein the heterologous gene segment is inserted in the HIV segment instead of the region of non-essential HIV nucleotide sequences wherein the non-essential nucleotides are in the 3' nef sequence of the HIV genome.

11. The vector of claim 4, heterologous gene segment is inserted in the HIV segment instead of the region of non-essential HIV nucleotide sequences region of the HIV genome wherein the non-essential HIV nucleotide sequences correspond to the 51 3' nucleotides in the env gene, the intervening nucleotides in the 3' direction until a KpnI site located 60 nucleotides 5' to the beginning of the 3' LTR.

* * * * *